United States Patent
Keshwani

(10) Patent No.: US 11,494,586 B2
(45) Date of Patent: Nov. 8, 2022

(54) TOMOGRAPHIC IMAGE MACHINE LEARNING DEVICE AND METHOD

(71) Applicant: FUJIFILM Corporation, Tokyo (JP)

(72) Inventor: Deepak Keshwani, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 66 days.

(21) Appl. No.: 17/000,372

(22) Filed: Aug. 24, 2020

(65) Prior Publication Data

US 2020/0387751 A1    Dec. 10, 2020

Related U.S. Application Data

(63) Continuation of application No. PCT/JP2019/007048, filed on Feb. 25, 2019.

(30) Foreign Application Priority Data

Feb. 27, 2018  (JP) .............................. JP2018-033451

(51) Int. Cl.
*G06K 9/62* (2022.01)
*G06T 7/00* (2017.01)
(Continued)

(52) U.S. Cl.
CPC ......... *G06K 9/6256* (2013.01); *G06K 9/6261* (2013.01); *G06T 7/0012* (2013.01);
(Continued)

(58) Field of Classification Search
CPC .. G06K 9/6256; G06K 9/3233; G06K 9/6261; G06K 9/4628; G16H 50/20;
(Continued)

(56) References Cited

U.S. PATENT DOCUMENTS 9,251,596 B2    2/2016  Rueckert et al.
2010/0128946 A1  5/2010  Fidrich et al.
(Continued)

FOREIGN PATENT DOCUMENTS

JP    2004097535    4/2004
JP    2006325629    12/2006
(Continued)

OTHER PUBLICATIONS

Bottger et al, Measuring the Accuracy of Object Detectors and Trackers (Year: 2017).*

(Continued)

*Primary Examiner* — Kenny A Cese
(74) *Attorney, Agent, or Firm* — JCIPRNET

(57) ABSTRACT

There are provided machine learning device and method which can prepare divided data suitable for machine learning from volume data for learning. A machine learning unit (15) calculates detection accuracy of each organ O(j,i) in a predicted mask Pj using a loss function Loss. However, the detection accuracy of the organ O(k,i) with a volume ratio A(k,i)<Th is not calculated. That is, in the predicted mask Pk, the detection accuracy of the organ O(k,i) with a volume ratio that is small to some extent is ignored. The machine learning unit (15) changes each connection load of a neural network (16) from an output layer side to an input layer side according to the loss function Loss.

10 Claims, 6 Drawing Sheets

(51) Int. Cl.
*G06T 11/00* (2006.01)
*G06V 10/25* (2022.01)

(52) U.S. Cl.
CPC ............ *G06T 11/003* (2013.01); *G06V 10/25* (2022.01); *G06T 2207/10072* (2013.01); *G06T 2207/20081* (2013.01); *G06T 2207/30004* (2013.01)

(58) Field of Classification Search
CPC ........ G16H 50/70; G16H 30/40; G06N 3/063; G06N 3/084; G06N 3/0454; A61B 6/032; A61B 6/5217; G06T 11/008; G06T 11/003; G06T 7/0012; G06T 2207/10072; G06T 2207/20081; G06T 2207/30004
See application file for complete search history.

(56) References Cited

U.S. PATENT DOCUMENTS

| | | | |
|---|---|---|---|
| 2014/0086465 A1 | 3/2014 | Wu et al. | |
| 2016/0110632 A1* | 4/2016 | Kiraly | G06V 10/267 382/128 |
| 2018/0025255 A1 | 1/2018 | Poole et al. | |
| 2018/0184997 A1 | 7/2018 | Tsukagoshi et al. | |

FOREIGN PATENT DOCUMENTS

| | | |
|---|---|---|
| JP | 2010119850 | 6/2010 |
| JP | 2013506478 | 2/2013 |
| JP | 2015530193 | 10/2015 |
| JP | 2017202321 | 11/2017 |
| JP | 2018011958 | 1/2018 |

OTHER PUBLICATIONS

"Office Action of Japan Counterpart Application" with English translation thereof, dated Apr. 6, 2021, p. 1-p. 4.

"International Search Report (Form PCT/ISA/210)" of PCT/JP2019/007048, dated May 21, 2019, with English translation thereof, pp. 1-5.

"Written Opinion of the International Searching Authority (Form PCT/ISA/237)" of PCT/JP2019/007048, dated May 21, 2019, with English translation thereof, pp. 1-7.

* cited by examiner

TOMOGRAPHIC IMAGE MACHINE LEARNING DEVICE AND METHOD

CROSS-REFERENCE TO RELATED APPLICATIONS

The present application is a Continuation of PCT International Application No. PCT/JP2019/007048 filed on Feb. 25, 2019 claiming priority under 35 U.S.C § 119(a) to Japanese Patent Application No. 2018-033451 filed on Feb. 27, 2018. Each of the above applications is hereby expressly incorporated by reference, in its entirety, into the present application.

BACKGROUND OF THE INVENTION

1. Field of the Invention

The present invention relates to a machine learning device and a machine learning method, and particularly relates to machine learning device and method for constructing a machine-learned model that performs classification (segmentation) of structures of an image.

2. Description of the Related Art

In the related art, there has been a technique of detecting anatomical feature points of specific organs by machine learning from three-dimensional medical image data (volume data) such as a computed tomography (CT) image to detect organs included in the volume data.

For example, in JP2017-202321A, by using a supervised machine learning algorithm, anatomical feature points included in volume data are extracted, a model indicating a three-dimensional positional relationship of anatomical feature points in the body and the extracted feature points are compared to optimize the extracted feature points, and a part is detected. Further, in a case where a plurality of organs are shown at one absolute position, positional information of a plurality of parts is assigned to one CT image. In this manner, for example, in a case where a CT image is divided into series, it is possible to divide the CT image into series for each part on the basis of the positional information.

SUMMARY OF THE INVENTION

In recent years, a discriminator that simultaneously extracts a plurality of organs from volume data by machine learning or the like is developed. That is, in a case where volume data is input to the discriminator, data in which a label such as "stomach", "lung", "bronchi", "liver", or "hepatic portal vein" is added to each of voxels constituting the volume data is output. Such a simultaneous labeling function is useful as preprocessing for a wide variety of applications.

The discriminator that simultaneously performs labeling of two or more organs prepares a number of sets of original volume data and voxels of each organ, which are manually labeled by a doctor or the like, included in the volume data, as ground truth data and completes a learned model by performing machine learning of the data.

Here, the volume data for learning has a very large capacity, and thus the volume data for learning is divided to be input to a machine learning process for the convenience of a memory size used in the machine learning, in some cases.

In case of three-dimensional CT image data, the data is divided in an axial direction by a certain number within a memory size limit. The divided data is data for learning. Here, in a case where the divided data includes only a part of the labeled organ, the data may adversely affect machine learning.

The invention is made in view of such problems, and an object of the invention is to provide machine learning device and method which can prepare divided data suitable for machine learning from volume data for learning.

A machine learning device according to a first aspect of the invention comprises a learning data input unit that receives an input of learning data including volume data of a tomographic image and labeling of a region in the volume data; a division unit that divides the learning data of which the input is received by the learning data input unit to create divided learning data; a learning exclusion target region discrimination unit that discriminates a learning exclusion target region which is a region to be excluded from a target of learning, from the divided learning data created by the division unit and the learning data; and a machine learning unit that performs machine learning of labeling of a region other than the learning exclusion target region discriminated by the learning exclusion target region discrimination unit, on the basis of the divided learning data created by the division unit.

In the machine learning device according to a second aspect of the invention, the learning exclusion target region discrimination unit compares a volume of the region labeled in the divided learning data created by the division unit and a volume of the region labeled in the learning data and discriminates the learning exclusion target region according to whether the volume is equal to or less than a threshold value.

The machine learning device according to a third aspect of the invention further comprises a detection accuracy calculation unit that calculates detection accuracy of a region other than the learning exclusion target region discriminated by the learning exclusion target region discrimination unit, in which the machine learning unit performs machine learning of the labeling of the region other than the learning exclusion target region on the basis of the divided learning data created by the division unit and the detection accuracy calculated by the detection accuracy calculation unit.

In the machine learning device according to a fourth aspect of the invention, the detection accuracy calculation unit calculates the detection accuracy on the basis of an average of Intersection over Union (IoU) between a predicted label and a ground truth label of each region.

In the machine learning device according to a fifth aspect of the invention, the division unit re-divides the learning data such that the entire learning exclusion target region is included.

In the machine learning device according to a sixth aspect of the invention, the division unit creates pieces of divided learning data having an overlapping portion.

In the machine learning device according to a seventh aspect of the invention, the tomographic image is a three-dimensional medical tomographic image, and the region includes an organ.

A machine learning method according to an eighth aspect of the invention, which is executed by a computer, comprises a step of receiving an input of learning data including volume data of a tomographic image and labeling of a region in the volume data; a step of dividing the learning data to create divided learning data; a step of discriminating a learning exclusion target region which is a region to be excluded from a target of learning, from the divided learning data and the learning data; and a step of performing machine learning of labeling of a region other than the learning exclusion target region on the basis of the divided learning data.

A machine learning program for causing a computer to execute the machine learning method and a machine-learned model obtained by machine learning by the machine learning program are also included in the invention.

With the invention, since the learning exclusion target region is discriminated from the divided learning data and machine learning of labeling of regions other than the learning exclusion target region is performed, it is possible to perform machine learning with high accuracy even from the divided data in which only a part of an organ is included.

DESCRIPTION OF THE PREFERRED EMBODIMENTS

Figure 1:
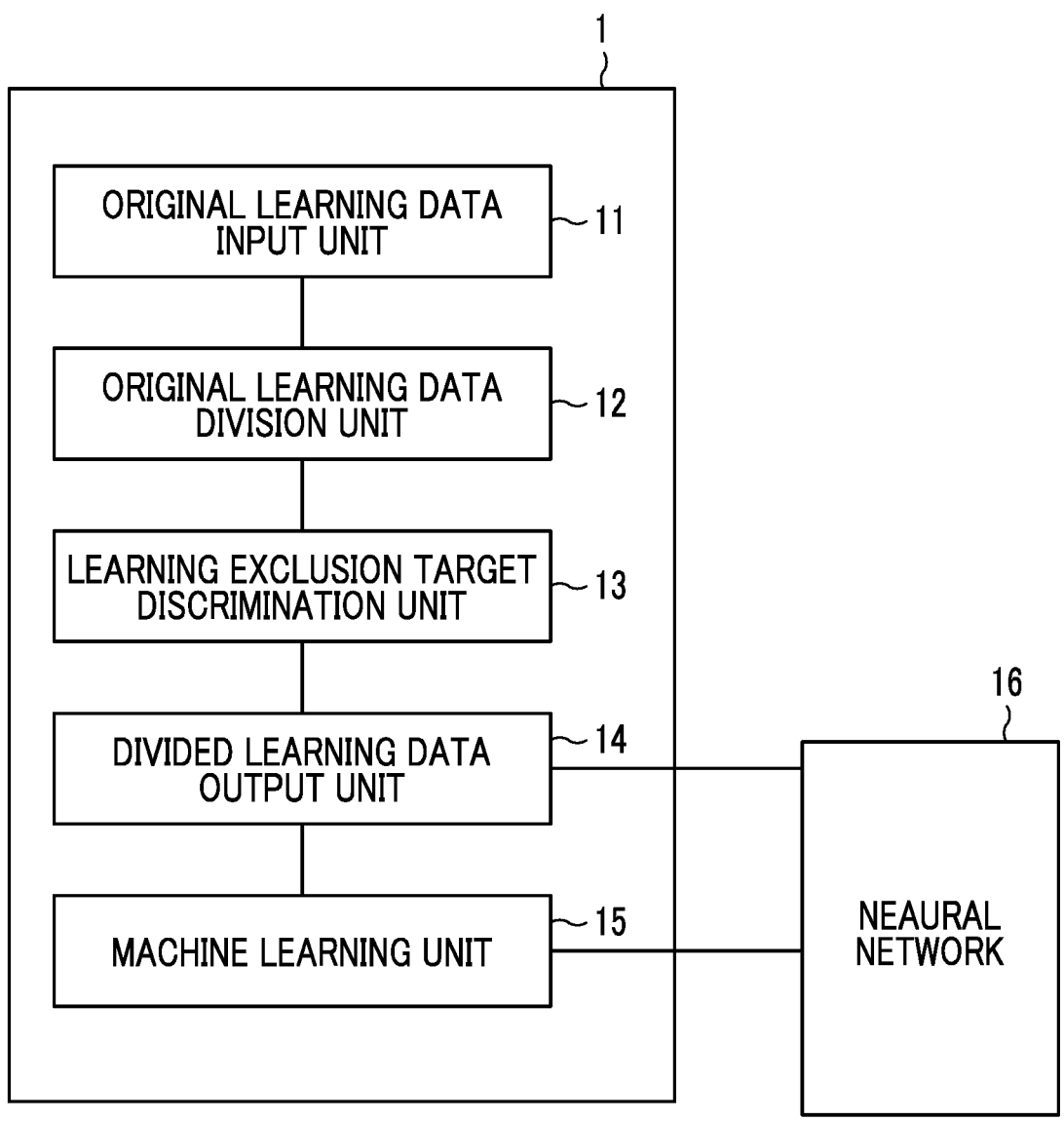
FIG. 1 is a schematic configuration diagram of a machine learning device.

FIG. 1 is a schematic configuration diagram of a machine learning device 1 according to a preferred embodiment of the invention. The machine learning device 1 comprises an original learning data input unit 11, an original learning data division unit 12, a learning exclusion target discrimination unit 13, a divided learning data output unit 14, and a machine learning unit 15. The machine learning device 1 is constituted by a computer comprising a processor such as a graphics processing unit (GPU), and each unit described above is realized by a program executed by a processor. The machine learning device 1 may include or may not include a neural network 16.

The original learning data input unit 11 receives an input of sets (original learning data) of volume data V consisting of a number of axial tomographic images (multi-slice images) and a ground truth mask G in which each pixel in an image is classified into the type (class) of an anatomical structure by a doctor or the like manually assigning (labeling) a ground truth label such as "lung", "bronchi", "blood vessel", "air filling pattern", and "others (background)" to each voxel included in the volume data.

Figure 2:
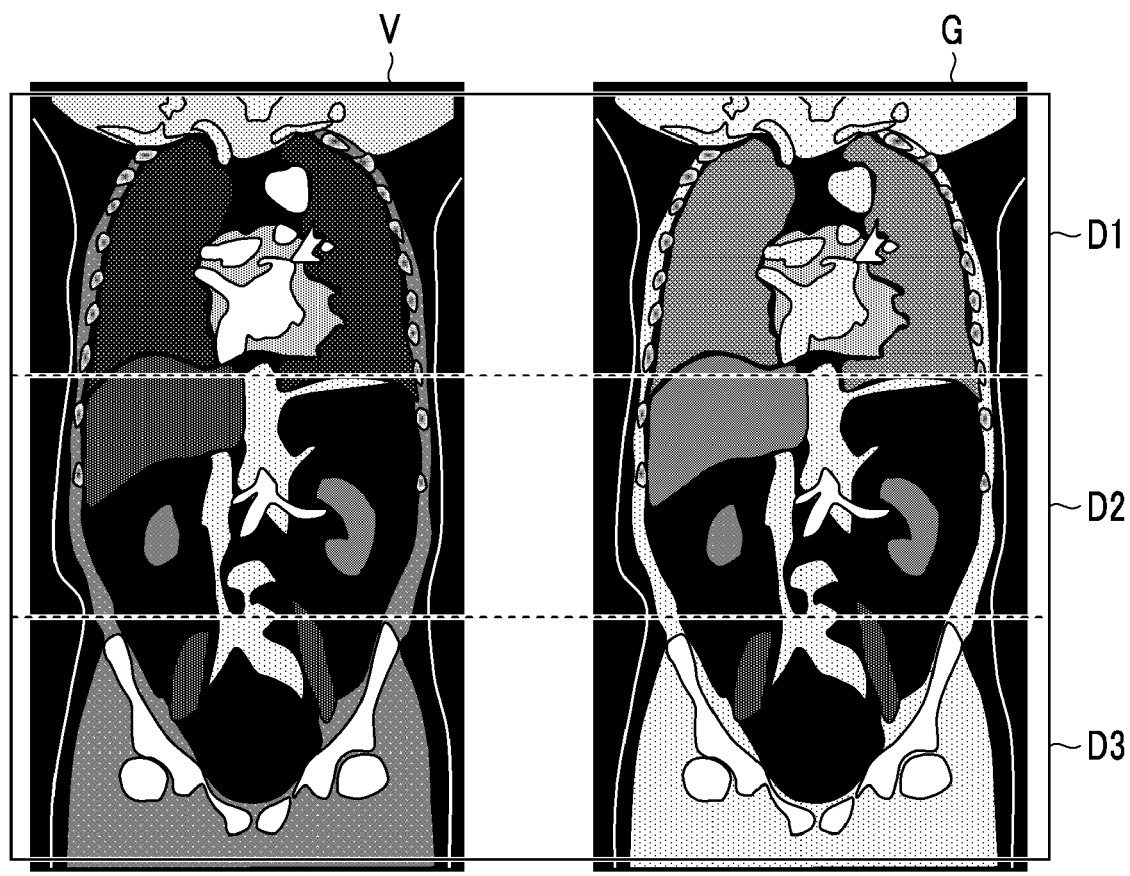
FIG. 2 is a conceptual explanatory diagram of divided learning data.

The original learning data division unit 12 divides (crops) the original learning data of which the input is received by the original learning data input unit 11, in the axial direction by a predetermined unit to create N pieces of divided learning data D1, D2, D3, . . . , and DN consisting of divided volume data V1, V2, V3, . . . , and VN and divided ground truth masks G1, G2, G3, . . . , and GN (refer to FIG. 2). The unit for division of the divided learning data D1, D2, D3, and the like depends on a hardware limit such as computing devices or a memory of the neural network 16. That is, the division unit depends on the amount of data that the neural network 16 can accept at one time.

Different two pieces of divided learning data may include an overlapping portion. Further, the original learning data may be divided not only in the axial direction but also in a sagittal direction or a coronal direction.

The learning exclusion target discrimination unit 13 calculates, from the volume data V, a total volume Vi of each organ Oi (i is an integer of 1 or more), and calculates a volume V(j,i) (i=1 to n(j)) of n(j) organs O(j,i) included in the divided ground truth mask Gj. O(j,i) is assigned with the same organ label as Oi. However, O(j,i) and Oi do not exactly match depending on the position of division.

Figure 3:
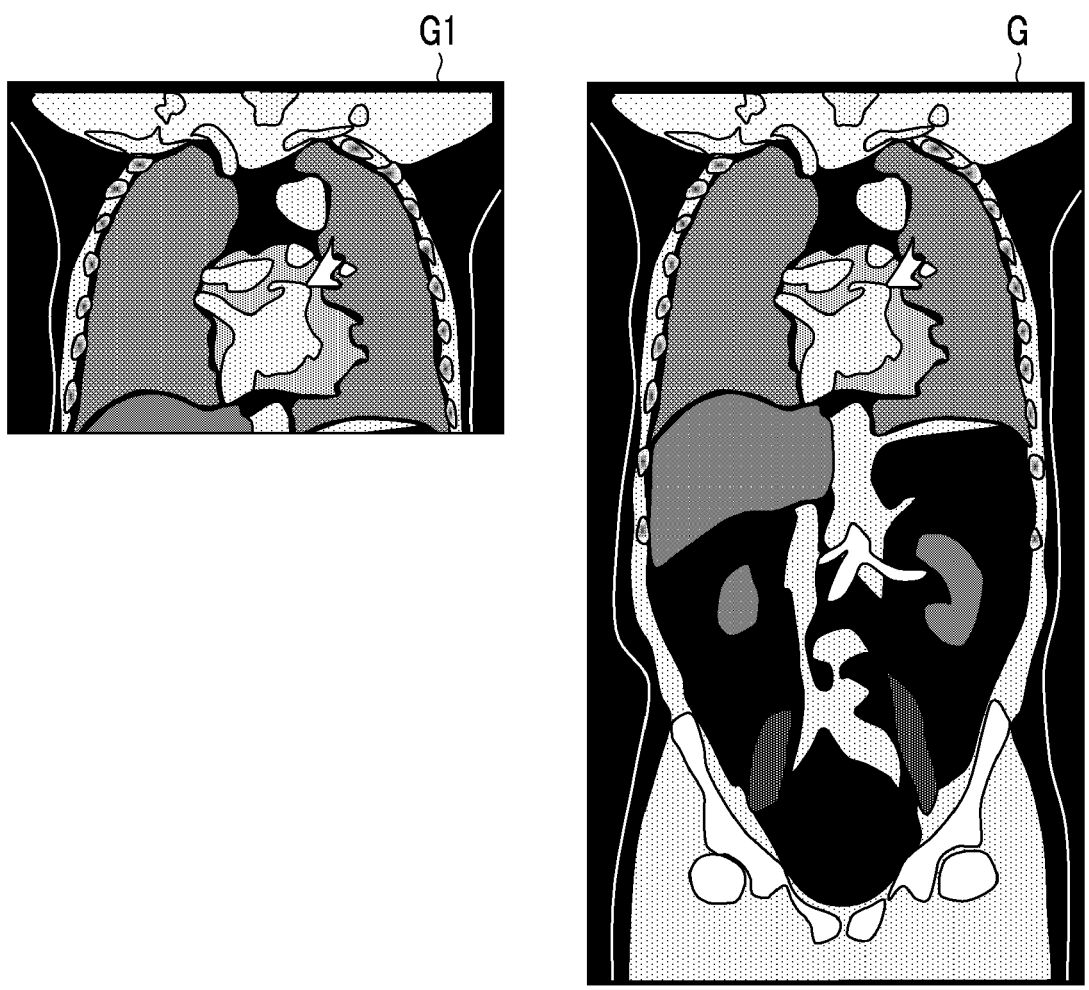
FIG. 3 is a conceptual explanatory diagram of divided ground truth data in which a labeling region of an organ is cut.

For example, as illustrated in FIG. 3, an organ O(1,1) with a label of "liver" in the divided ground truth mask G1 has a shape in which a part of an organ O1 with a label of "liver" in the ground truth mask G is cut.

The learning exclusion target discrimination unit 13 calculates a volume ratio A(j,i)=V(j,i)/Vi(<1) of the organ O(j,i) in the divided ground truth mask Gj to the organ Oi in the ground truth mask G.

The learning exclusion target discrimination unit 13 discriminates whether the entire organ Oi included or only a part of the organ Oi is included in the divided learning data Dj on the basis of the volume ratio A(j,i)=V(j,i)/Vi of the organ Oi in the divided ground truth mask Gj.

Specifically, the learning exclusion target discrimination unit 13 discriminates whether the volume ratio A(j,i) falls below a predetermined threshold value Th (for example, Th=0.9 or the like, or substantially 1 or a value near 1). The learning exclusion target discrimination unit 13 discriminates the divided learning data Dk having a subscript k with A(k,i)<Th as a learning exclusion target of the organ Oi. Hereinafter, the organ Oi with A(k,i)<Th in the divided learning data Dk is expressed as O(k,i).

Instead of the volume ratio, an area ratio of the organ Oi included in the divided learning data Dj may be calculated from the divided learning data Dj in the sagittal direction or coronal direction, and whether only a part of the organ Oi is included in the divided learning data may be discriminated on the basis of the area ratio.

The divided learning data output unit 14 outputs the divided learning data Dj subjected to the discrimination of the learning exclusion target discrimination unit 13, to the machine learning unit 15.

The machine learning unit 15 causes the neural network 16 to perform machine learning on the basis of the divided learning data Dj output from the divided learning data output unit 14.

The neural network 16 is a multi-layer classifier configured by a convolutional neural network (CNN) or the like.

The machine learning of the neural network 16 by the machine learning unit 15 uses backpropagation (error propagation method). The backpropagation is a method of comparing teacher data for the input data with actual output data obtained from the neural network 16 to change each connection load from an output layer side to an input layer side on the basis of the error.

Figure 4:
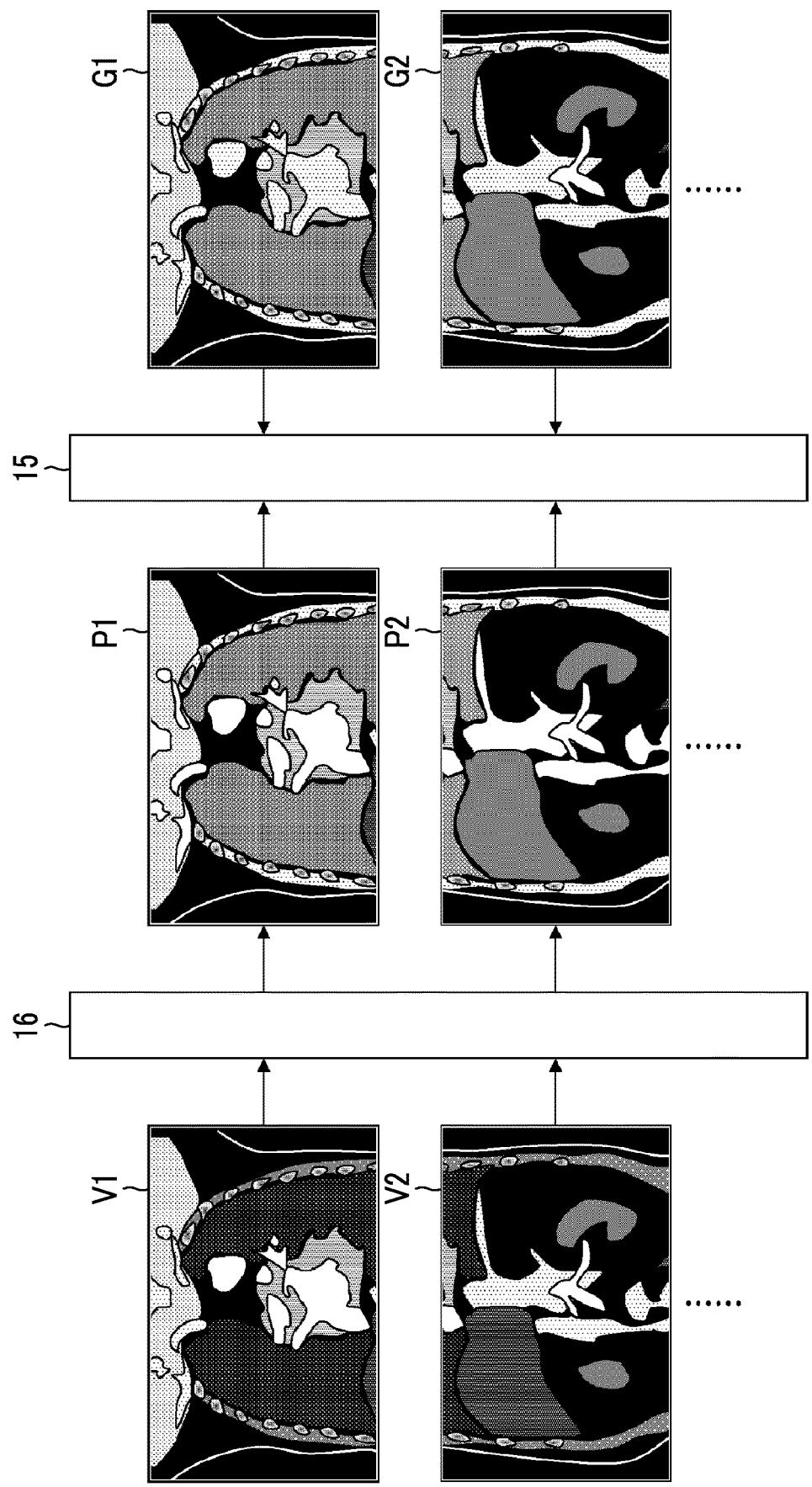
FIG. 4 is a conceptual explanatory diagram of backpropagation performed for each piece of divided learning data Dj.

Specifically, as illustrated in FIG. 4, first, the neural network 16 classifies structures in the divided volume data Vj by assigning a label such as "lung", "bronchi", "blood vessel", "air filling pattern", and "others (background)" to each voxel (pixel in case of two-dimensional data) of the divided volume data Vj included in the divided learning data Dj according to a learned model obtained by some machine learning. In this manner, a predicted mask Pj which is a set of voxels subjected to the labeling of each organ is obtained for each divided learning data Dj.

The machine learning unit 15 compares the predicted mask Pj with the divided ground truth mask Gj as the teacher data to perform backpropagation of the neural network 16 on the basis of the error. That is, the backpropagation of the neural network 16 is performed for each divided learning data Dj.

However, in a case where the organ O(k,i) as the learning exclusion target is included in a predicted mask Pk corresponding to the divided learning data Dk, the machine learning unit 15 does not perform backpropagation of labeling of the organ O(k,i). The details will be described below.

Figure 5:
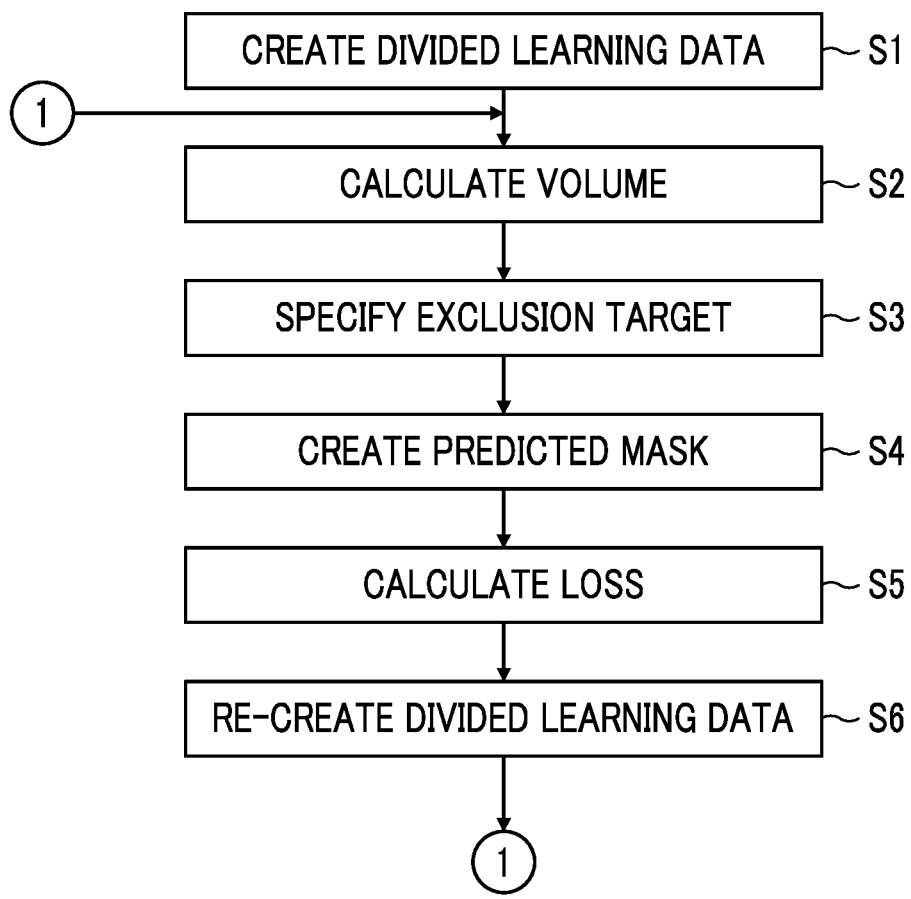
FIG. 5 is a flowchart of a machine learning process.

FIG. 5 is a flowchart of a machine learning process using the divided learning data Dj. A program for causing a processor of the machine learning device 1 to execute the machine learning process is stored in a computer-readable tangible storage medium such as a random access memory (RAM) of the machine learning device 1. The medium in which the program is stored may be a non-transitory computer-readable recording medium such as a hard disk, a compact disk (CD), a Digital Versatile Disk (DVD), and various semiconductor memories.

First, in S1 (divided learning data creation step), the original learning data division unit 12 creates N divided learning data D1, D2, . . . , and DN from the original learning data that is received by the original learning data input unit 11. N is an integer of 2 or more. FIG. 2 illustrates a case of N=4. The unit for division of the learning data depends on the memory capacity and the processing performance of the GPU, and any amount less than the maximum amount that the divided learning data can be processed is set as a unit for division.

In S2 (volume calculation step), the learning exclusion target discrimination unit 13 calculates a volume ratio A(j, i)=V(j,i)/Vi of each organ O(j,i) from the divided ground truth mask Gj and the ground truth mask G.

In S3 (exclusion target specifying step), the learning exclusion target discrimination unit 13 determines whether the volume ratio A(j,i) is less than the predetermined threshold value Th. In case of j=k, and in case of A(k,i)<Th, the learning exclusion target discrimination unit 13 discriminates that the learning exclusion target in the divided learning data Dk is the organ O(k,i).

In S4 (predicted mask creation step), the neural network 16 inputs the divided volume data Vj of the divided learning data Dj to create the predicted mask Pj of each of n(j) organs O(j,i). Here, j=1, 2, . . . , and N.

In S5 (loss calculation step), the machine learning unit 15 calculates the detection accuracy of each organ O(j,i) in the predicted mask Pj using a loss function Loss. However, in case of j=k, the detection accuracy of the organ O(k,i) is not calculated. That is, in the predicted mask Pk, the detection accuracy of the organ O(k,i) with a volume ratio that is small to some extent is ignored.

Specifically, in the predicted mask Pj, the detection accuracy acc(j,i) is calculated for each of n(j) types of organs O(j,i) except for the organ O(k,i) as the learning exclusion target, and the average value thereof is regarded as the loss function Loss(j) corresponding to the divided learning data Dj.

Loss(j)=Avg(acc(j,i)) (i=1, 2, . . . , n(j), where i≠(k) and acc(k,i)=0). acc(j,i) is the Intersection over Union (IoU) of each organ O(j,i) in the predicted mask Pj. That is, the IoU is a value obtained by dividing the number of voxels the intersection of a set Pr(i) of the organ O(j,i) in the predicted mask Pj and a set Ht of the organ O(j,i) in the divided ground truth mask Gj, by the number of voxels of a union of the set Pr(i) and the set Ht. As the detection accuracy of each organ O(j,i) in the divided volume data Vj is increased, acc(j,i) approaches 1. However, in a case where there are many organs with a low detection accuracy, even in a case where the detection accuracy of another organ is high, the loss function Loss does not approach 1. The detection accuracy of the organ of which the volume ratio is less than the threshold value is not reflected in the value of the loss function Loss in the first place.

The expression for calculating the detection accuracy is not limited to the above description. In general, the expression can be represented by Expression (1).

$$acc(i) = f1(Pr(i) \cap Ht)/f2(Pr(i) \cup Ht) \quad (1)$$

f1 is a function using Expression (2) as a parameter.

$$Pr(i) \cap Ht \quad (2)$$

f2 is a function using Expression (3) as a parameter.

$$Pr(i) \cup Ht \quad (3)$$

For example, a value obtained by multiplying the IoU by a constant (such as 100 times) or a Dice coefficient may be used as acc (i).

In S6 (backpropagation step), the machine learning unit 15 changes each connection load of the neural network 16 from the output layer side to the input layer side according to the loss function Loss.

In S7 (divided learning data creation step), the original learning data division unit 12 re-creates the divided learning data Dk. In this case, the original learning data division unit 12 re-divides the original learning data such that the entire organ O(k,i) is included in the divided learning data Dk. However, the unit for re-division is also constrained by hardware resources. The process returns to S2, and for the divided learning data Dk, the predicted mask Pk of each organ including the organ O(k,i) is created.

Figure 6:
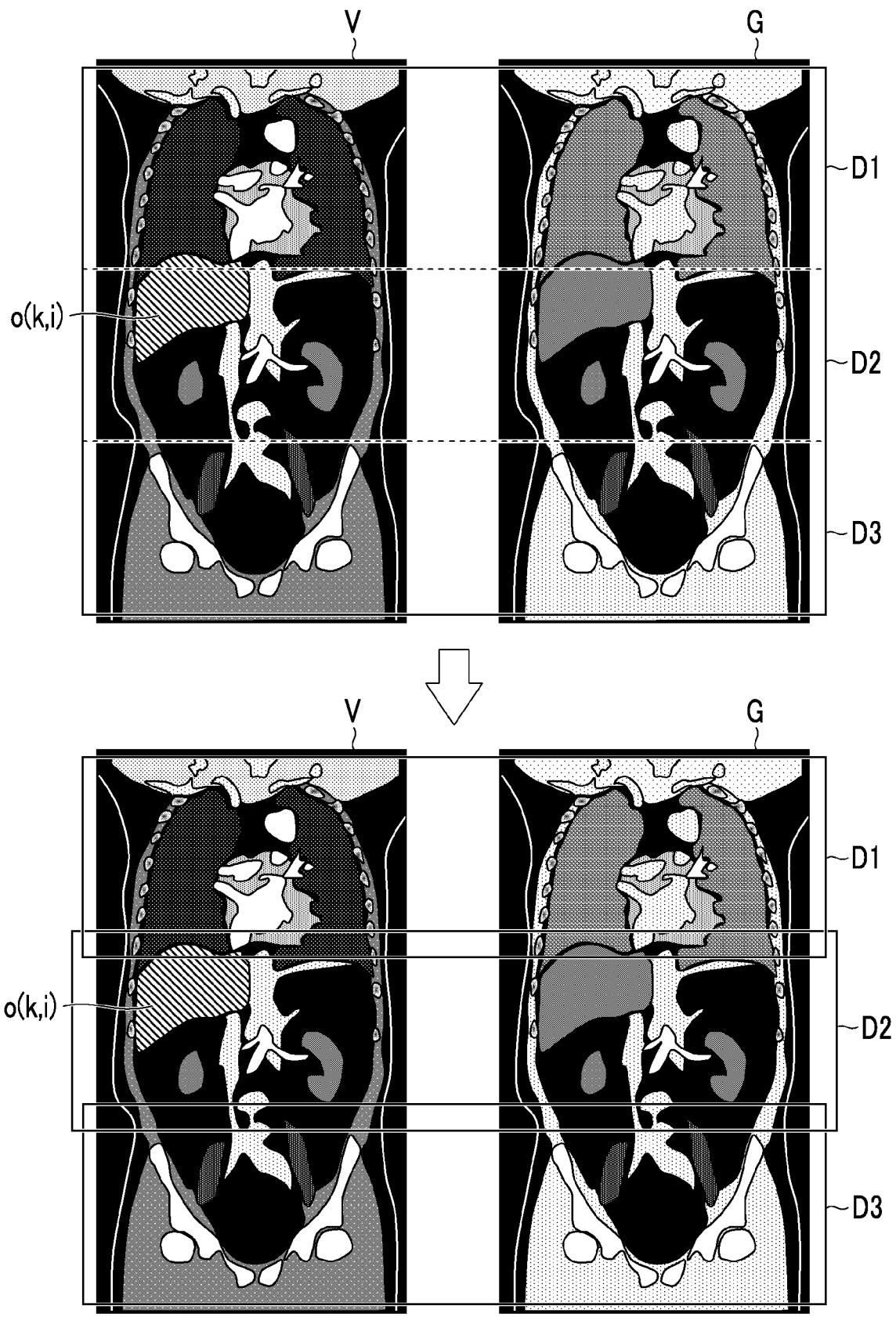
FIG. 6 is a conceptual explanatory diagram of re-division of learning data.

FIG. 6 is an example of re-creation of the divided learning data Dk. Here, the divided learning data D2 created once is shifted toward the head along the axial (body axis) direction. In this manner, for the organ O(k,i) as the learning exclusion target, machine learning with high accuracy can be performed on the basis of the shifted divided learning data D2. S2 to S7 described above can be repeated any number of times. Accordingly, division is performed again such that any organ Oi is included in any divided learning data, and further, backpropagation based on the loss function may be performed each time division is performed.

Thus, it is possible to perform backpropagation to improve the detection accuracy of any organ regardless of the volume of the organ. However, in a case where an organ having a volume smaller than the threshold value is included in the divided learning data, the detection accuracy of the organ is not reflected in the loss function. Therefore, it is possible to prevent that the detection accuracy of a part of an organ which is cut due to the division of the original learning data is reflected in the loss function to adversely affect the backpropagation.

Further, the organ cut due to the division of the learning data can be subjected to the calculation of detection accuracy and the backpropagation by re-division of the learning data.

EXPLANATION OF REFERENCES

1: machine learning device
11: original learning data input unit

12: original learning data division unit
13: learning exclusion target discrimination unit
14: divided learning data output unit
15: machine learning unit
16: neural network

What is claimed is:

1. A machine learning device comprising:
a neural network;
a machine learning unit;
a processor configured to function as:
   a learning data input unit that receives an input of learning data, the learning data including volume data of a tomographic image and labeling of a first region in the volume data;
   a division unit that divides the learning data received by the learning data input unit to create divided learning data, wherein the divided learning data includes a second region, and a labeling of the second region corresponds to the labeling of the first region;
   a learning exclusion target region discrimination unit that discriminates a learning exclusion target region which is a region to be excluded from a target of learning, from the divided learning data created by the division unit and the learning data;
wherein the machine learning unit trains the neural network to perform labeling of a region other than the learning exclusion target region discriminated by the learning exclusion target region discrimination unit by machine learning, on the basis of the divided learning data created by the division unit,
wherein the learning exclusion target region discrimination unit compares a volume of the second region labeled in the divided learning data to a volume of the first region labeled in the learning data, and sets the second region as the learning exclusion target region to be excluded from the target of learning when a volume ratio of the second region to the first region is equal to or less than a predetermined threshold value.

2. The machine learning device according to claim 1, the processor is further configured to function as:
   a detection accuracy calculation unit that calculates detection accuracy of a region other than the learning exclusion target region discriminated by the learning exclusion target region discrimination unit,
   wherein the machine learning unit performs the labeling of the region other than the learning exclusion target region by machine learning, on the basis of the divided learning data created by the division unit and the detection accuracy calculated by the detection accuracy calculation unit.

3. The machine learning device according to claim 2, wherein the detection accuracy calculation unit calculates the detection accuracy on the basis of an average of Intersection over Union (IoU) between a predicted label and a ground truth label of each region.

4. The machine learning device according to claim 1, wherein the division unit re-divides the learning data to create another divided learning data in which a number of the learning exclusion target region is reduced.

5. The machine learning device according to claim 1, wherein the division unit creates pieces of divided learning data having an overlapping portion.

6. The machine learning device according to claim 1, wherein the tomographic image is a three-dimensional medical tomographic image, and the first region includes an organ.

7. A machine learning method executed by a computer, the machine learning method comprising:
   a step of receiving an input of learning data including volume data of a tomographic image and labeling of a first region in the volume data;
   a step of dividing the learning data to create divided learning data, wherein the divided learning data includes a second region, and a labeling of the second region corresponds to the labeling of the first region;
   a step of discriminating a learning exclusion target region which is a region to be excluded from a target of learning, from the divided learning data and the learning data; and
   a step of training a neural network to perform labeling of a region other than the learning exclusion target region by machine learning, on the basis of the divided learning data,
wherein a volume of the second region labeled in the divided learning data is compared to a volume of the first region labeled in the learning data, and the second region is set as the learning exclusion target region to be excluded from the target of learning when a volume ratio of the second region to the first region is equal to or less than a predetermined threshold value.

8. A machine-learned model obtained by machine learning by the machine learning method according to claim 7.

9. A non-transitory computer-readable recording medium that records thereon, computer commands which cause a computer to execute the machine learning method according to claim 7 in a case where the computer commands are read by the computer.

10. A machine learning device comprising:
a neural network;
a machine learning unit;
a processor configured to function as:
   a learning data input unit that receives an input of learning data, the learning data including volume data of a tomographic image and labeling of a first region in the volume data;
   a division unit that divides the learning data received by the learning data input unit to create divided learning data, wherein the divided learning data includes a second region, and a labeling of the second region corresponds to the labeling of the first region;
   a learning exclusion target region discrimination unit that discriminates a learning exclusion target region which is a region to be excluded from a target of learning, from the divided learning data created by the division unit and the learning data;
wherein the machine learning unit trains the neural network to perform labeling of a region other than the learning exclusion target region discriminated by the learning exclusion target region discrimination unit by machine learning, on the basis of the divided learning data created by the division unit,
wherein the learning exclusion target region discrimination unit compares an area of the second region labeled in the divided learning data to an area of the first region labeled in the learning data, and sets the second region as the learning exclusion target region to be excluded from the target of learning when an area ratio of the second region to the first region is equal to or less than a predetermined threshold value.

* * * * *